United States Patent
Brown, Jr. et al.

(10) Patent No.: US 8,523,875 B2
(45) Date of Patent: Sep. 3, 2013

(54) GRAFT CALIPER MARKING DEVICE

(75) Inventors: Charles Henry Brown, Jr., Wellesley, MA (US); Michael Charles Ferragamo, Foster, RI (US); William Richard Davis, Hingham, MA (US)

(73) Assignee: Smith & Nephew, Inc., Memphis, TN (US)

( * ) Notice: Subject to any disclaimer, the term of this patent is extended or adjusted under 35 U.S.C. 154(b) by 62 days.

(21) Appl. No.: 13/270,967

(22) Filed: Oct. 11, 2011

(65) Prior Publication Data

US 2013/0090664 A1   Apr. 11, 2013

(51) Int. Cl.
*A61B 5/107* (2006.01)

(52) U.S. Cl.
USPC ............... 606/102; 33/511; 33/512

(58) Field of Classification Search
USPC .................... 606/102; 33/511, 512
See application file for complete search history.

(56) References Cited

U.S. PATENT DOCUMENTS

| 4,718,850 | A | * | 1/1988 | Knebelman | 433/72 |
| 5,383,874 | A | * | 1/1995 | Jackson et al. | 606/1 |
| 5,681,333 | A | | 10/1997 | Burkhart et al. | |
| 2006/0207118 | A1 | | 9/2006 | Kim | |

FOREIGN PATENT DOCUMENTS

WO  2004006811  1/2004

OTHER PUBLICATIONS

International Search Report mailed Jan. 15, 2013 in corresponding International Patent Application No. PCT/US2012/059296.

* cited by examiner

*Primary Examiner* — Kevin T Truong
*Assistant Examiner* — Christian Sevilla
(74) *Attorney, Agent, or Firm* — Chapin IP Law, LLC

(57) ABSTRACT

A graft caliper provides for a first member having a first pick at its distal end and its proximal end attached to a handle. A second member of the graft caliper is disposed above the first member and has a second pick at its distal end that extends beyond the first pick. The proximal end of the second member is attached to an adjuster which causes the second member to move from a first position to a second position in order to change a distance the second pick extends beyond the first pick. The graft caliper provides for an indication of at least one metric for describing the distance the second pick extends beyond the first pick and places an identifier on a surface of bone representing the location of a tunnel to be formed through a femur, tibia or any other anatomical structure.

6 Claims, 5 Drawing Sheets

GRAFT CALIPER MARKING DEVICE

BACKGROUND

Reconstructive bone and ligament surgery often involves drilling bone tunnels into skeletal members to attach connective elements such as ligament and tendon grafts, as well as various artificial replacements and/or attachments for articulated joints. Careful placement and subsequent drilling ensures maximum joint mobility from the resulting reconstruction.

A common anterior cruciate ligament (ACL) reconstruction technique involves the drilling of bone tunnels into the tibia and the femur in order to place an ACL graft in almost the same position as the torn ACL. The free ends of a suture loop are then passed through the tunnel of the tibia, up through the femoral tunnel, and then out through the skin of the thigh. The sutures of the graft are placed through the eye of the needle and the graft is pulled into position up through the tibial tunnel and then up into the femoral tunnel. The graft is held under tension as it is fixed in place using interference screws, spiked washers, buttons, posts and/or staples.

Anatomic placement of the ACL graft is critical to the success of the ACL reconstruction. In fact, the most commonly cited error in ACL reconstruction is nonanatomic tunnel placement, with an improperly placed femoral tunnel being the root cause in most cases. When the femoral tunnel is placed in a position that is too anterior, the result can be a graft that experiences constraint in flexion and laxity in extension. When the femoral tunnel is placed too posteriorly, a loss of fixation due to posterior wall blowout may be experience along with a constraint in extension due to nonisometric tunnel position. Placement of the femoral tunnel that is too central results in a graft that may not restore the rotational component of stability provided by the ACL, thereby leading to a persistently positive pivot shift, despite objective anterior/posterior stability.

SUMMARY

Determining an accurate position of an ACL femoral tunnel continues to be a challenge for surgeons performing ACL reconstructions. Offset guides and templates are often utilized to assist with accurate placement of the femoral tunnel. However, these devices require multiple steps and often require the surgeon to use both hands or assistance from another person.

Techniques and configurations discussed herein significantly overcome the deficiencies of current approaches in determining the proper placement of bone tunnels during surgical procedures, such as ACL reconstructive surgery. As will be discussed further, certain specific embodiments herein are directed to a Graft Caliper Marking Device (hereinafter "graft caliper") that provides a simple approach to accurately measure and mark an anatomic location that can be performed by a single person. Such embodiment discussed herein are especially useful for determining a proper location and measurement of a femoral tunnel and a tibial tunnel prior to ACL reconstructive surgery.

The graft caliper discussed herein provides for a first member having a first pick at its distal end and its proximal end attached to a handle. A second member of the graft caliper is disposed above the first member. The second member has a second pick at its distal end whereby the second pick extends beyond the first pick. The proximal end of the second member is attached to an adjuster, which is in mechanical communication with the first member. Manipulation of the adjuster causes the second member to move from a first position to a second position in order to change a distance the second pick extends beyond the first pick. The graft caliper also provides for an indication of at least one metric for describing the distance the second pick extends beyond the first pick.

In one embodiment, manipulation of the adjuster causes the graft caliper's second member to slide over the first member from the first position to the second position while the first pick remains stationary. The indication for describing the distance that the second pick extends beyond the first pick is revealed as the second member slides over the first member. In addition, at least one of the first pick and the second pick creates an identifier on a bone surface upon contact such that the identifier represents a placement of a tunnel to be formed through a femur and/or a tibia.

It is understood that various embodiments of the graft caliper can be made from plastic and/or metal and can be powered by electrical radio frequency or electrocautery wand. Further, various embodiments of the graft caliper can a single handed sliding device that can be shaped to match bone contours and landmarks in conjunction with the electrical RF and/or electrocautery wand.

In yet another embodiment, the first pick of the graft caliper is placed against a first portion of a surface of a bone. While maintaining a current placement of the first pick, the second pick is extended beyond the first pick toward a second portion of a the surface of the bone. Upon placing the second pick against the second portion of the surface of the bone, the graft caliper provides a measurement of a distance the second pick currently extends from the current placement of the first pick. In addition, an identifier can be disposed on the surface of the bone with at least one of the first pick and the second pick. The identifier thereby represents the location of a tunnel to be formed through a femur, tibia or any other anatomical structure.

In yet another embodiment, the graft caliper's first member can have a hook for placement against a portion of bone and a second member slidably disposed beneath the first member. The second member can have a pick that is slidably withdrawn, away from the first member's hook, from a first position to a second position. The graft caliper can further provide a locking mechanism to hold the pick at the second position.

BRIEF DESCRIPTION OF THE DRAWINGS

The foregoing and other objects, features and advantages of the invention will be apparent from the following description of particular embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION

Figure 1:
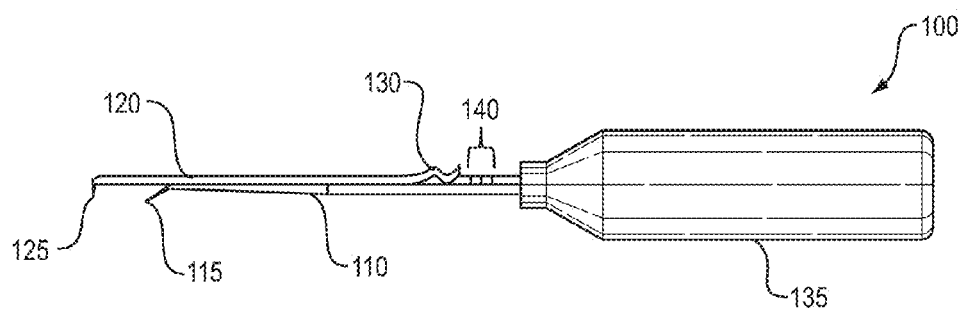
FIG. 1 shows a perspective view of the graft caliper according to embodiments herein.

Methods and apparatus described herein are directed toward a graft caliper 100. FIG. 1 shows a perspective view of the graft caliper 100 according to embodiments herein.

The graft caliper 100 has a first member 110 having a first pick 115 at its distal end and its proximal end attached to a handle 135. A second member 120 of the graft caliper 100 is disposed above the first member 110. The second member 120 has a second pick 125 at its distal end whereby the second pick 125 extends beyond the first pick 115. The proximal end of the second member 120 is attached to an adjuster 130, which is in mechanical communication with the first member 110. Manipulation of the adjuster 130 causes the second member 120 to move from a first position to a second position in order to change a distance the second pick 125 extends beyond the first pick 115. The graft caliper 100 also provides for an indication(s) 140 of at least one metric for describing the distance the second pick 125 extends beyond the first pick 115. Also, the graft caliper 100 places an identifier on the surface of the bone with at least one of the first pick 115 and the second pick 125. The identifier thereby represents the location of a femoral tunnel and a tibial tunnel prior to ACL reconstructive surgery. The graft caliper 100 can also be utilized for obtaining measurements and locations with regard to any other anatomical structure as well.

Manipulation of the adjuster 130 causes the second member 120 to slide over the first member 110 from the first position to the second position while the first pick 115 remains stationary. Thus, once the first pick 115 of the first member 110 has been placed against a first portion of a surface of a bone, a user can manipulate the adjuster 130 in order to cause the second pick 125 of the second member 120 to move toward a second portion of the surface of the bone.

Once both the respective first pick 115 and second pick 125 has been set upon the surface of the bone, the graft caliper 100 provides an indication(s) 140 of the distance that the second pick 125 extends beyond the first pick 115. Such indication(s) 140 can be discerned via the adjuster's 130 placement on the graft caliper 100 with respect to measurement indicia placed on a visible surface of the first member 110 and/or the second member 120. Further, the first pick 115 and/or the second pick 125 create(s) an identifier on the bone wherein the identifier represents a placement of a center of the tunnel to be formed through the bone.

Figure 2:
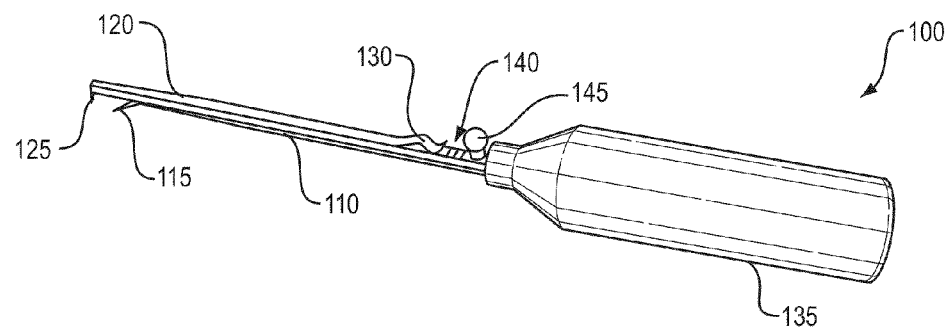
FIG. 2 shows a perspective view of the graft caliper with an ink reservoir to provide ink to mark a surface of a bone according to embodiments herein.

FIG. 2 shows a perspective view of the graft caliper 100 with an ink reservoir to provide ink to mark a surface of a bone according to embodiments herein.

The graft caliper 100 provides an ink reservoir, such as an ink bulb 155, that houses ink or any other kind of marking solution. The first and/or second member 110, 120 of the graft caliper 100 has an internal cavity, such as an ink tunnel through which the ink can pass. Once the first and/or second pick 115, 125 has been placed on the surface of the bone, and the user wishes to mark the surface of the bone with the corresponding pick's 115, 125 current placement, the user can manipulate the ink reservoir such that the ink flows through the pick's internal cavity, out from a tip of the corresponding pick 115, 125 and onto the surface of the bone. In various embodiments, the ink mark (or any other kind of identifier) represents a placement of a center of a tunnel to be formed (or drilled) through the bone, such as a femur or tibia for example.

In one embodiment, an electrocautery wand is disposed on at least a portion of the first pick 115 and/or the second pick 125. Once the corresponding pick 115, 125 is placed upon the surface of the bone, the electrocautery wand burns a mark (or identifier) on the surface of the bone to indicate the placement of the tunnel to be formed through the bone.

In yet another embodiment, the first pick 115 and/or the second pick 125 is charged with electrical radio frequency. Once the pick 115, 125 is placed on the surface of the bone, the charged corresponding pick 115, 125 burns a surface of the bone to create a mark indicating the placement of the tunnel to be formed through the bone.

Figure 3:
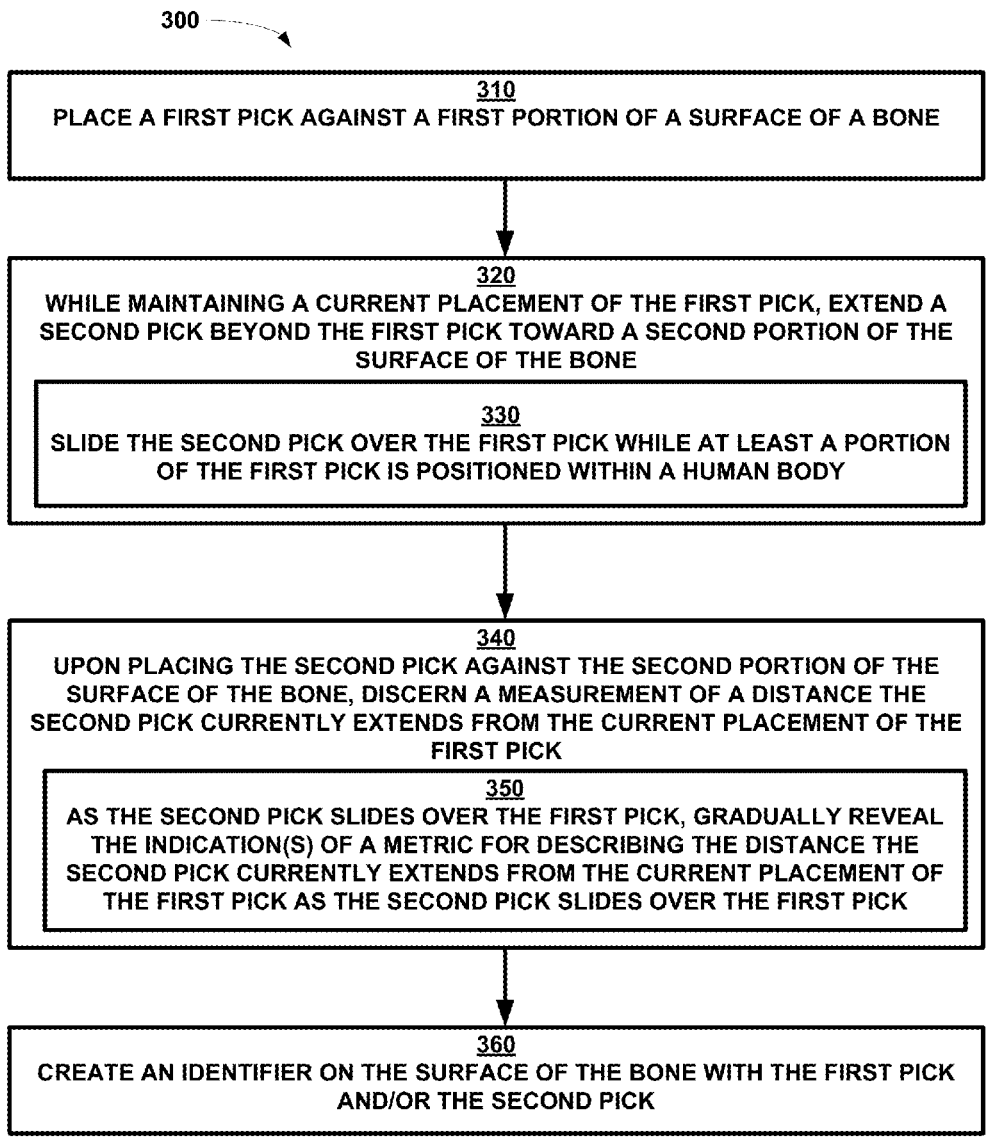
FIG. 3 shows a flowchart of steps performed to create an identifier on a surface of a bone in order to represent a location of a tunnel to be formed through the bone according to embodiments herein.

FIG. 3 shows a flowchart 300 of steps performed to create an identifier on a surface of a bone in order to represent a location of a tunnel to be formed through the bone according to embodiments herein.

At step 310, place a first pick 115 against a first portion of a surface of a bone. The bone can be a portion of a tibia and/or a portion of a femur. The first pick 115 can be placed against the first portion of a surface of a bone in order to ascertain placement of a tunnel to be formed within the bone in preparation for ACL reconstructive surgery.

At step 320, while maintaining a current placement of the first pick 115, extend a second pick 125 beyond the first pick 115 toward a second portion of the surface of the bone.

At step 330, slide the second pick 125 over the first pick 115 while at least a portion of the first pick 115 is positioned within a human body.

At step 340, upon placing the second pick 125 against the second portion of the surface of the bone, discern a measurement of a distance the second pick 125 currently extends from the current placement of the first pick 115.

At step 350, as the second pick 125 slides over the first pick 115, gradually reveal the indication(s) 140 of the metric for describing the distance the second pick 125 currently extends from the current placement of the first pick 115 as the second pick 125 slides over the first pick 115.

At step 360, create an identifier on the surface of the bone with the first pick 115 and/or the second pick 125. It is understood that in various embodiments, the identifier can be a divot etched onto the surface of the bone, a mark burned onto the surface of the bone or a mark created by use of a marking solution (such as ink).

Figure 4:
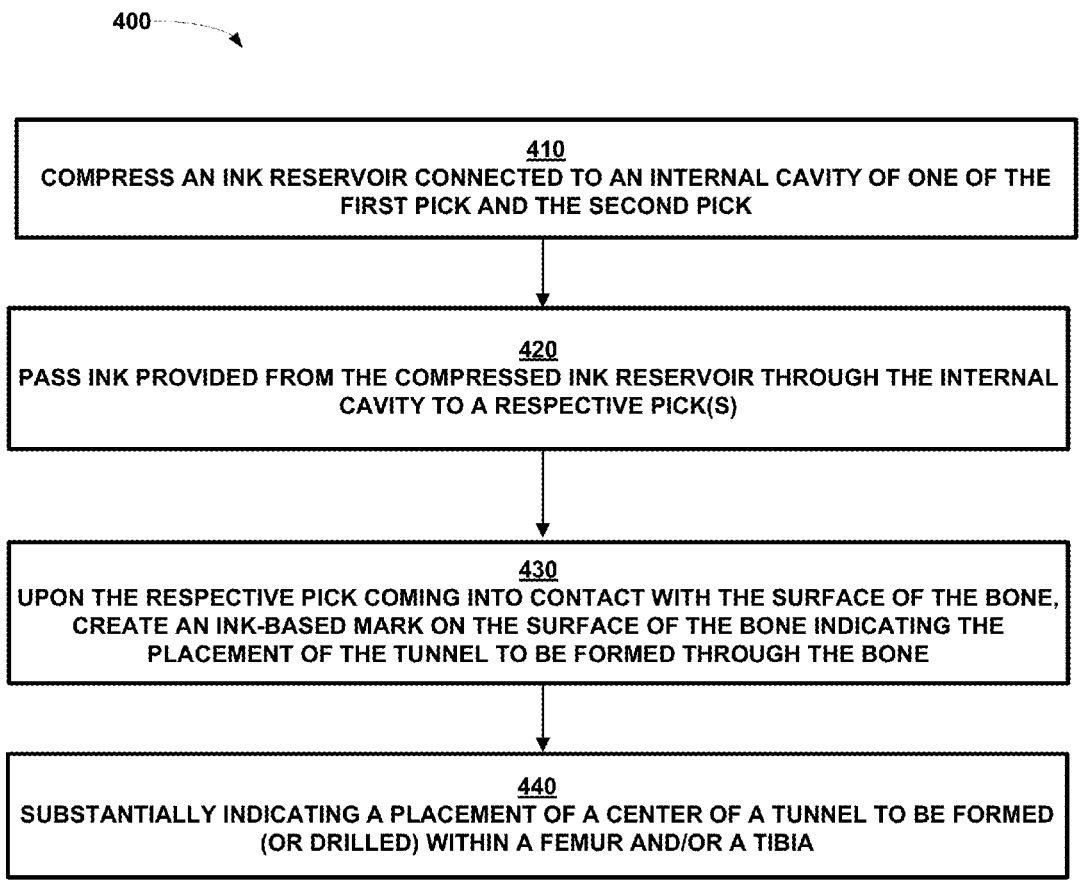
FIG. 4 shows a flowchart of steps performed to create an ink mark on a surface of a bone in order to represent a location of a tunnel to be formed through the bone according to embodiments herein.

FIG. 4 shows a flowchart 400 of steps performed to create an ink mark on a surface of a bone in order to represent a location of a tunnel to be formed through the bone according to embodiments herein.

At step 410, compress an ink reservoir connected to an internal cavity of one of the first pick 115 and the second pick 125. In one embodiment, the ink reservoir can be an ink bulb 155 in contact with an internal cavity of at least one of the first pick 115 and the second pick 125. The ink bulb 155 can be squeezable, such that when the ink bulb 155 is squeezed, ink that is stored within the ink bulb 155 is pushed into the internal cavity.

At step 420, pass ink provided from the compressed ink reservoir through the internal cavity to a respective pick(s). The ink passes from the internal cavity and through an opening of the respective pick(s).

At step 430, upon the respective pick coming into contact with the surface of the bone, create an ink-based mark on the surface of the bone indicating the placement of the tunnel to be formed through the bone.

At step 440, substantially indicating a placement of a center of a tunnel to be formed (or drilled) within a femur and/or a tibia.

Figure 5:
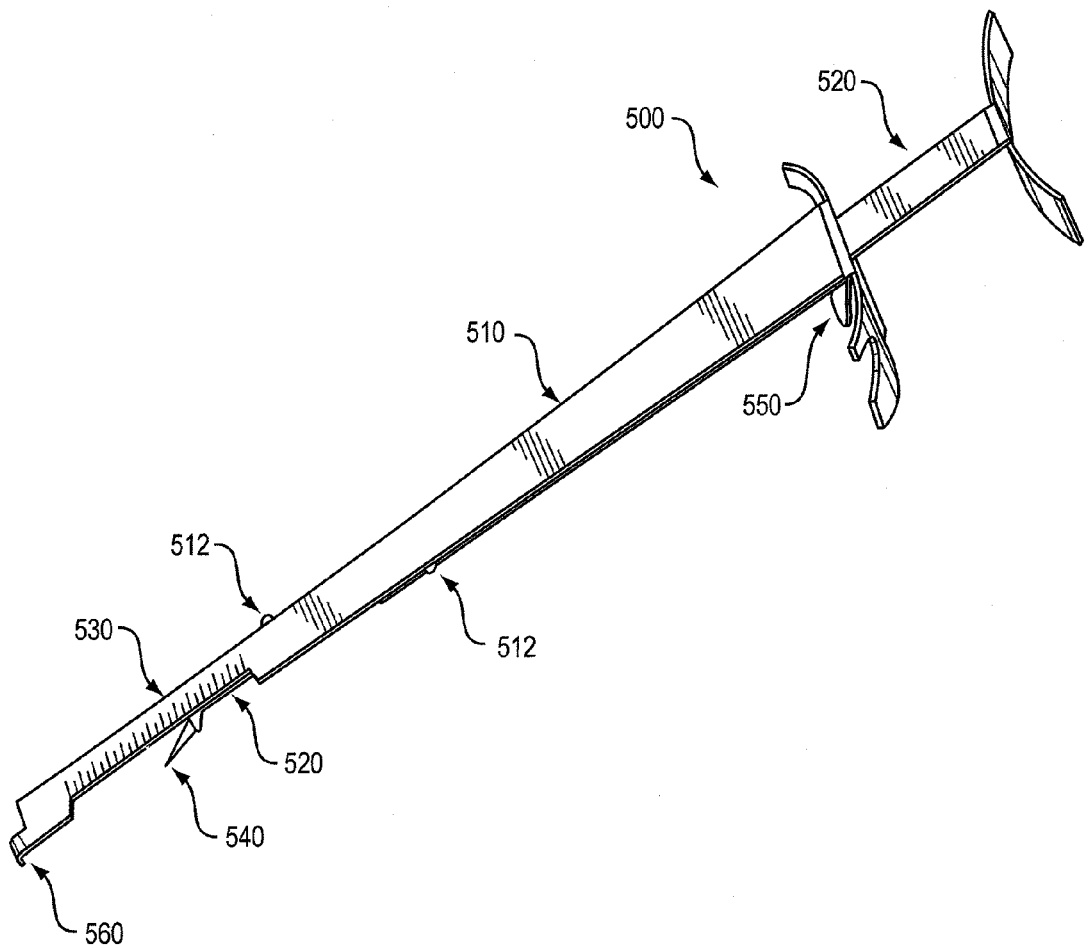
FIG. 5 shows a perspective view of an alternative embodiment of a graft caliper according to embodiments herein.

Turning now to FIG. 5, a perspective view of an alternative embodiment of the graft caliper 500 is shown. The alternative graft caliper 500 includes a first member 510. The first member 510 provides two hooks 512 and 516 that curl around a second member 520. The second member 520 is slidably disposed beneath the first member 510. The alternative graft caliper 500 can be inserted into a joint such that a hook portion 560 of the first member 510 is placed against a portion of a bone (such as a back wall of a femur). It is understood that the dimensions of the alternative graft caliper 500 are such that the alternative graft caliper 500 can be inserted into joint from the hook portion 560 up to a particular hook 516.

Once the hook portion 560 is places against a portion of bone, the second member 520 can be slide away from the hook portion 560 such that the pick 540 of the second member 520 slides beneath the first member 510 from a first position to a second position. Once the pick 540 reaches the second position, a locking mechanism 550 can be activated to be hold the second member 520 in place. A distance measurement can be determined with respect to the locked pick's 540 placement with respect to measurement indicia 530 provided by the first member 510.

While this invention has been particularly shown and described with references to preferred embodiments thereof, it will be understood by those skilled in the art that various changes in form and details may be made therein without departing from the spirit and scope of the present application as defined by the appended claims. Such variations are intended to be covered by the scope of this present application. As such, the foregoing description of embodiments of the present application is not intended to be limiting, the full scope rather being conveyed by the appended claims.

What is claimed is:

1. A caliper device for locating a placement of a tunnel to be formed through at least a portion of a bone, comprising:
    a first member having a distal end comprising a first pick;
    a second member disposed above the first member, the second member having a distal end comprising a second pick extending beyond the first pick and a proximal end attached to an adjuster, wherein manipulation of the adjuster causes the second member to move from a first position to a second position in order to change a distance the second pick extends beyond the first pick;
    wherein at least a portion of at least one of the first pick and the second pick are charged with electrical radio frequency, wherein a charged corresponding pick burns a surface of the bone upon contact to create at least a mark indicating the placement of the tunnel to be formed through the bone; and
    an indication of at least one metric for describing the distance the second pick extends beyond the first pick.

2. The caliper device of claim 1, wherein the manipulation of the adjuster causes the second member to slide over the first member from the first position to the second position while the first pick remains stationary.

3. The caliper device of claim 1, wherein at least one of the first pick and the second pick creates an identifier on a surface of the bone upon contact with the bone, wherein the identifier represents a placement of a center of the tunnel to be formed through the bone.

4. The caliper device of claim 3, wherein the identifier comprises one of: a marking on the surface of the bone, a divot etched into the surface of the bone and a burned portion of the surface of the bone.

5. The caliper device of claim 3, wherein the identifier represents the placement of a center of the tunnel to be formed through one of: at least a portion of the femur and at least a portion of the tibia.

6. A caliper device for locating a placement of a tunnel to be formed through at least a portion of one of a femur and a tibia for ligament reconstructive surgery, comprising:
    a first member having a distal end comprising a first pick and a proximal end attached to a handle;
    a second member slidably disposed above the first member, the second member having a distal end comprising a second pick extending beyond the first pick while at least a portion of the first pick is positioned within a human body;
    wherein at least a portion of at least one of the first pick and the second pick are charged with electrical radio frequency, wherein a charged corresponding pick burns a surface of the bone upon contact to create at least a mark indicating the placement of the tunnel to be formed through the bone;
    an adjuster adjustably secured to the first member and connected to a proximal end of the second member, wherein manipulation of the adjuster causes the second member to slide from a first position to a second position in order to change a distance the second pick extends from the first pick; and
    at least one metric disposed on a top surface of the first member revealed as the second member slides over the first member, the at least one metric for describing at least a portion of distance the second pick extends beyond the first pick.

* * * * *